United States Patent
Yajima

(10) Patent No.: US 10,627,620 B2
(45) Date of Patent: Apr. 21, 2020

(54) HEAD-MOUNTED DISPLAY DEVICE, METHOD OF CONTROLLING HEAD-MOUNTED DISPLAY DEVICE, AND COMPUTER PROGRAM

(71) Applicant: SEIKO EPSON CORPORATION, Tokyo (JP)

(72) Inventor: Kenro Yajima, Matsumoto (JP)

(73) Assignee: SEIKO EPSON CORPORATION, Tokyo (JP)

(*) Notice: Subject to any disclaimer, the term of this patent is extended or adjusted under 35 U.S.C. 154(b) by 279 days.

(21) Appl. No.: 14/921,613

(22) Filed: Oct. 23, 2015

(65) Prior Publication Data
US 2016/0140773 A1   May 19, 2016

(30) Foreign Application Priority Data
Nov. 17, 2014 (JP) ................. 2014-232750

(51) Int. Cl.
*G06T 19/00* (2011.01)
*A61B 5/16* (2006.01)
(Continued)

(52) U.S. Cl.
CPC .......... *G02B 27/0093* (2013.01); *A61B 3/113* (2013.01); *A61B 5/163* (2017.08);
(Continued)

(58) Field of Classification Search
CPC ........ G06T 19/006; A61B 3/113; A61B 5/163
See application file for complete search history.

(56) References Cited

U.S. PATENT DOCUMENTS

| | | | |
|---|---|---|---|
| 2014/0191946 A1* | 7/2014 | Cho | G02B 27/017 345/156 |
| 2015/0085251 A1* | 3/2015 | Larsen | G06K 9/00604 351/206 |

(Continued)

FOREIGN PATENT DOCUMENTS

| | | |
|---|---|---|
| JP | 2000-102036 A | 4/2000 |
| JP | 2005-100366 A | 4/2005 |

(Continued)

OTHER PUBLICATIONS

Yoshida, et al., "A Technique of High-Precise Depth Correction in Stereoscopic Display", TVRSJ, vol. 5, No. 3, pp. 1019-1026, 2000.

*Primary Examiner* — Matthew Salvucci
(74) *Attorney, Agent, or Firm* — Oliff PLC

(57) ABSTRACT

A head-mounted display device with which a user can visually recognize a virtual image and an outside scene includes an image display unit configured to cause the user to visually recognize the virtual image, a detecting unit configured to cause the image display unit to form the virtual image for causing the user to visually recognize a mark on any standard coordinate on a three-dimensional space, calculate a gazing point coordinate on the three-dimensional space representing a gazing point of the user gazing at the mark, and detect a shift between the standard coordinate and the gazing point coordinate, and an augmented-reality processing unit configured to cause the image display unit to form the virtual image including a virtual object to be displayed with respect to a real object actually present in a real world, the virtual object being arranged using the detected shift.

17 Claims, 10 Drawing Sheets

(51) Int. Cl.
  *A61B 3/113* (2006.01)
  *G02B 27/00* (2006.01)
  *G02B 27/01* (2006.01)

(52) U.S. Cl.
  CPC .......... *G02B 27/017* (2013.01); *G06T 19/006* (2013.01); *G02B 2027/014* (2013.01); *G02B 2027/0138* (2013.01); *G02B 2027/0185* (2013.01); *G02B 2027/0187* (2013.01)

(56) References Cited

U.S. PATENT DOCUMENTS

| | | |
|---|---|---|
| 2015/0288944 A1 | 10/2015 | Nistico et al. |
| 2015/0316981 A1* | 11/2015 | Sellen ................ G06K 9/0061 345/156 |
| 2016/0086338 A1* | 3/2016 | Nagamatsu ............ G06T 7/80 348/78 |
| 2016/0267708 A1 | 9/2016 | Nistico et al. |

FOREIGN PATENT DOCUMENTS

| | | |
|---|---|---|
| JP | 2005-128901 A | 5/2005 |
| WO | 2014-033306 A1 | 3/2014 |

\* cited by examiner

HEAD-MOUNTED DISPLAY DEVICE, METHOD OF CONTROLLING HEAD-MOUNTED DISPLAY DEVICE, AND COMPUTER PROGRAM

BACKGROUND

1. Technical Field

The present invention relates to a head-mounted display device.

2. Related Art

There is known a technique called augmented reality (AR) for additionally presenting information to a real object, which is an object actually present in a real world, using a computer. The information displayed additionally to the real object in the augmented reality is called "virtual object" as well. A function of the augmented reality is implemented in, for example, a head mounted display (hereinafter referred to as "HMD" or "head-mounted display device" as well).

The HMD picks up an image of an outside scene with a camera, recognizes the image obtained by the image pickup, and generates or acquires a virtual object. A transmissive HMD, which does not block a visual field of a user in a mounted state of the HMD, causes the user to visually recognize only a virtual image including the virtual object. The user can experience the augmented reality by viewing both of the real object in the real world and the virtual object represented by the virtual image.

When the augmented reality is implemented in the transmissive HMD, to reduce a visual sense of discomfort given to the user, it is preferable to align the position of the real object visually recognized by the user and the position of the virtual object visually recognized by the user. The "position" includes a distance from the user and positions in the horizontal direction and the vertical direction within the visual field of the user. Therefore, in the related art, the position of the real object and the position of the virtual object are aligned by causing the left and right eyes of the user to visually recognize a virtual image including the virtual object given with a parallax.

However, human eyes have individual differences. In other words, positions of eyes, a shape of eyeballs, positions of parts related to the visual sense in the eyes (e.g., lenses, retinas, and central pits), and the like are different in each person. Therefore, even if the left and right eyes of the user are caused to visually recognize the virtual image including the virtual object given with the parallax in order to align the position of the real object and the position of the virtual object, if users are different, a shift occurs in positions of the virtual object visually recognized by the users. JP-A-2005-100366 (Patent Literature 1) describes a technique for detecting a visual line direction of a patient in a non-contact manner by image-processing a face image of the patient acquired by a video camera.

JP-A-2005-128901 (Patent Literature 2) is also an example of the related art.

In order to reduce the visual sense of discomfort given to the user in the augmented reality processing, it is preferable to determine the position of the virtual object taking into account the individual difference of the eyes. In this regard, the techniques described in Patent Literatures 1 and 2 do not take into account at all that the individual difference of the eyes is taken into account in the augmented reality processing.

Therefore, there is a demand for a head-mounted display device capable of implementing augmented reality processing that takes into account the individual difference of the eyes.

SUMMARY

An advantage of some aspects of the invention is to solve at least a part of the problems described above, and the invention can be implemented as the following aspects.

(1) An aspect of the invention provides a head-mounted display device with which a user can visually recognize a virtual image and an outside scene. The head-mounted display device includes: an image display unit configured to cause the user to visually recognize the virtual image; a detecting unit configured to cause the image display unit to form the virtual image for causing the user to visually recognize a mark on any standard coordinate on a three-dimensional space, calculate a gazing point coordinate on the three-dimensional space representing a gazing point of the user gazing at the mark, and detect a shift between the standard coordinate and the gazing point coordinate; and an augmented-reality processing unit configured to cause the image display unit to form the virtual image including a virtual object to be displayed with respect to a real object actually present in a real world, the virtual object being arranged using the detected shift.

With the head-mounted display device according to this aspect, the shift detecting unit can detect a shift between the standard coordinate of the mark formed on the three-dimensional space and the gazing point coordinate representing the gazing point of the user gazing at the mark. This "shift" is a shift between a gazing point of a standard user gazing at the mark and a gazing point of an actual user of the head-mounted display device gazing at the mark and is a shift caused by an individual difference of the eyes of the actual user. The augmented-reality processing unit arranges the virtual object to be displayed with respect to the real object using the shift between the standard coordinate and the gazing point coordinate detected by the shift detecting unit (i.e., a shift caused by the individual difference of the eyes of the actual user). As a result, it is possible to provide the head-mounted display device capable of implementing the augmented reality processing that takes into account the individual difference of the eyes.

(2) In the head-mounted display device according to the aspect described above, the shift detecting unit may calculate, as the shift between the standard coordinate and the gazing point coordinate, an angle difference between a standard vector connecting a coordinate of the mark in image data transmitted to the image display unit and the standard coordinate and a gazing point vector connecting the coordinate of the mark in the image data transmitted to the image display unit and the gazing point coordinate.

With the head-mounted display device according to this aspect, the shift detecting unit can define the shift between the standard coordinate and the gazing point coordinate as an angle difference between a "standard vector" that can be identified as a vector connecting the central pit and the center of the lens of the eye of the standard user and a "gazing point vector" that can be identified as a vector connecting the central pit and the center of the lens of the eye of the actual user.

(3) In the head-mounted display device according to the aspect described above, the angle difference may include an angle difference of a roll angle, an angle different of a pitch angle, and an angle difference of a yaw angle.

With the head-mounted display device according to this aspect, the shift detecting unit can calculate an angle difference between the standard vector and the gazing point vector concerning each of an x axis, a y axis, and a z axis in a rectangular coordinate on the three-dimensional space.

(4) The head-mounted display device according to the aspect described above may further include an outside-scene-image acquiring unit configured to acquire at least two outside scene images corresponding to the left and right eyes of the user. The shift detecting unit may guide the user to point the mark and calculate the gazing point coordinate on the basis of the pointing in the at least two outside scene images acquired by the outside-scene-image acquiring unit.

With the head-mounted display device according to this aspect, the shift detecting unit can calculate the gazing point coordinate using at least two outside scene images acquired by the outside-scene-image acquiring unit (e.g., a stereo camera) generally mounted on the head-mounted display device.

(5) The head-mounted display device according to the aspect described above may further include: an outside-scene-image acquiring unit configured to acquire an outside scene image in a visual line direction of the user; and a distance acquiring unit configured to acquire a distance to any target object. The shift detecting unit may guide the user to point the mark and calculate the gazing point coordinate on the basis of the pointing in the outside scene image acquired by the outside-scene-image acquiring unit and the distance to the target object acquired by the distance acquiring unit.

With the head-mounted display device according to this aspect, when the outside-scene-image acquiring unit is capable of acquiring only one outside scene image, the shift detecting unit can calculate the gazing point coordinate concurrently using the distance to the target object acquired by the distance acquiring unit.

(6) In the head-mounted display device according to the aspect described above, the shift detecting unit may repeatedly execute, with respect to a different plurality of marks having a different plurality of standard coordinates, a series of processing for causing the user to visually recognize the mark on the standard coordinate, calculating the gazing point coordinate, and detecting a shift between the standard coordinate and the gazing point coordinate. The augmented-reality processing unit may use, in the arrangement of the virtual object, a plurality of shifts respectively detected concerning the different plurality of standard coordinates.

With the head-mounted display device according to this aspect, the augmented-reality processing unit arranges the virtual object using the plurality of shifts respectively detected concerning the different plurality of standard coordinates. Therefore, it is possible to improve accuracy of the individual difference of the eyes taken into account in the augmented reality processing.

(7) In the head-mounted display device according to the aspect described above, the shift detecting unit may execute the series of processing using, as the mark, any indication formed by any application in the head-mounted display device.

With the head-mounted display device according to this aspect, the shift detecting unit can execute, using, as the mark, any indication formed by any application in the head-mounted display device, on the background of the any application, the series of processing for detecting a shift between the standard coordinate and the gazing point coordinate. As a result, it is possible to reduce labor of the user.

(8) In the head-mounted display device according to the aspect described above, the shift detecting unit may cause, by giving a parallax between the virtual image visually recognized by the user with the right eye and the virtual image visually recognized by the user with the left eye, the user to visually recognize the mark on the standard coordinate.

With the head-mounted display device according to this aspect, the shift detecting unit can easily cause, using the principle of triangulation, the image display unit to form the virtual image for causing the user to recognize the mark on the standard coordinate.

Not all of the plurality of components in the aspects of the invention are essential. In order to solve a part or all of the problems or attain a part or all of the effects described in this specification, it is possible to appropriately perform, concerning a part of the plurality of components, a change, deletion, replacement with a new component, and partial deletion of limitation contents. In order to solve a part or all of the problems or attain a part or all of the effects described in this specification, it is also possible to combine a part or all of the technical features included in one aspect of the invention with a part or all of the technical features included in the other aspects of the invention to form an independent aspect of the invention.

For example, one aspect of the invention can be implemented as a device including a part or all of the three components of the image display unit, the shift detecting unit, and the augmented-reality processing unit. That is, the device may or may not include the image display unit. The device may or may not include the shift detecting unit. The device may or may not include the augmented-reality processing unit. Such a device can be implemented as, for example, a head-mounted display device. However, the device can also be implemented as devices other than the head-mounted display device. A part or all of the technical features of the head-mounted display device according to the aspects can be applied to the device. For example, an object of the device according to the aspect of the invention is to implemente augmented reality processing that takes into account the individual difference of the eyes. However, besides, a reduction in the size of the device, improvement of convenience, a reduction in costs in device manufacturing, resource saving, facilitation of manufacturing, and the like are demanded for the device.

Note that the invention can be implemented in various forms. The invention can be implemented in forms of, for example, a head-mounted display device, a control method for the head-mounted display device, a system including the head-mounted display device, a computer program for implementing the method, the device, and the system, and a storage medium having the computer program stored therein.

BRIEF DESCRIPTION OF THE DRAWINGS

The invention will be described with reference to the accompanying drawings, wherein like numbers reference like elements.

DESCRIPTION OF EXEMPLARY EMBODIMENTS

A. Embodiment
A-1. Configuration of a Head-mounted Display Device

Figure 1:
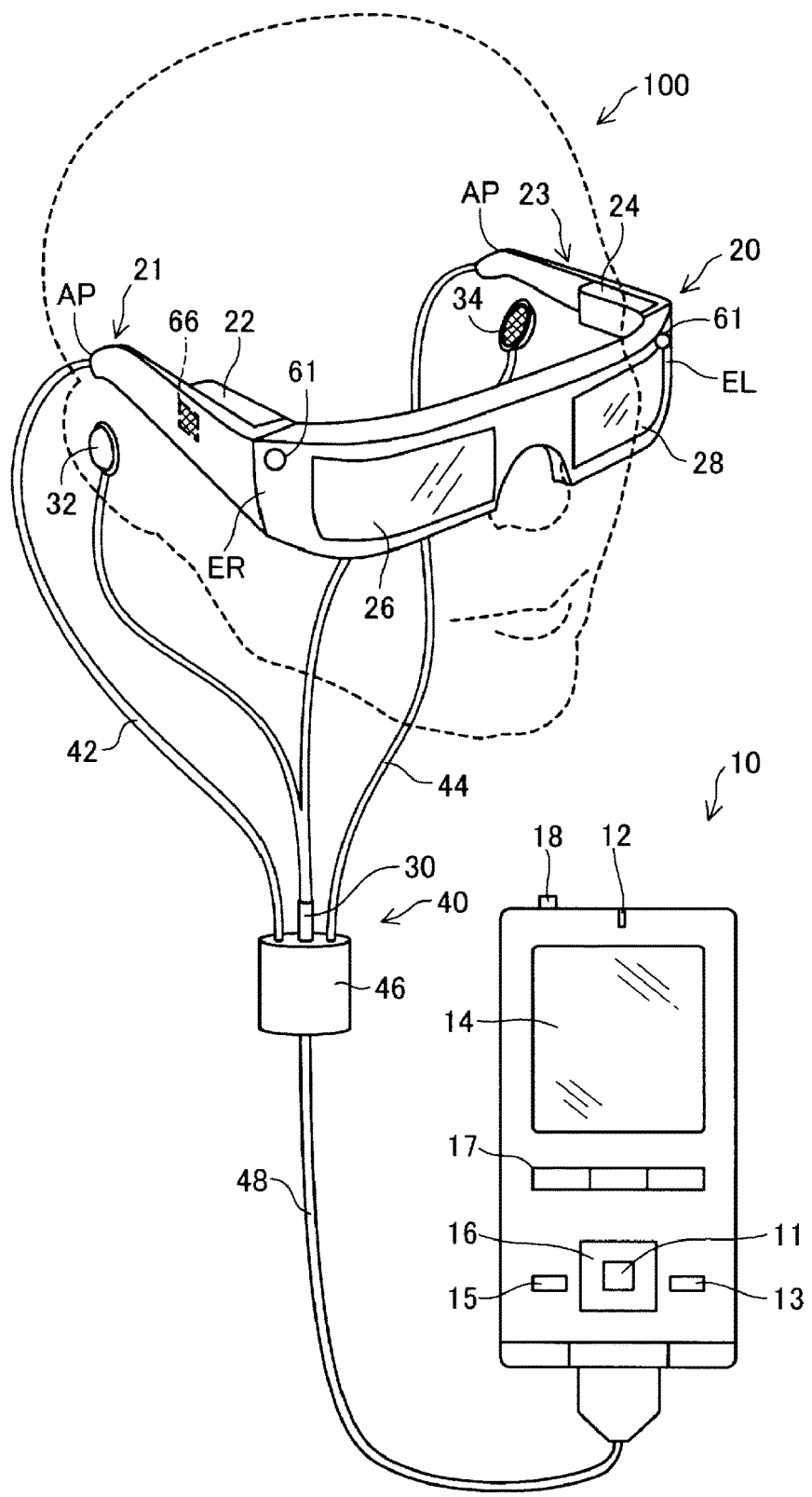
FIG. 1 is an explanatory diagram showing the schematic configuration of a head-mounted display device in an embodiment of the invention.

FIG. 1 is an explanatory diagram showing the schematic configuration of a head-mounted display device in an embodiment of the invention. A head-mounted display device 100 in this embodiment is a display device mounted on a head and is referred to as head mounted display (HMD) as well. The HMD 100 is a head-mounted display device of an optical transmission type with which a user is capable of directly visually recognizing an outside scene simultaneously with visually recognizing a virtual image.

The HMD 100 in this embodiment can perform augmented reality (AR) processing for adding information to a "real object", which is an object actually present in a real world, using a CPU of the HMD 100. The object means any person, any animal or plant, any object (including an artificial object and a natural object), and the like. In the augmented reality processing, information displayed additionally to the real object is referred to as "virtual object".

In this embodiment, "additionally" has meanings including all meanings described below.
  Add information to the real object using the virtual object.
  Highlight the real object using the virtual object.
  Delete or attenuate information (a color, a shape, etc.) of the real object using the virtual object.
  Combination of any two or more of the addition, the highlighting, the deletion, and the attenuation.

Note that the real object and the virtual object displayed additionally to the real object may or may not have a relation.

In the augmented reality processing, the HMD 100 in this embodiment causes the user to visually recognize only a virtual image including the virtual object. The user can experience augmented reality by viewing both of the real object transmitted through the HMD 100 and the virtual object represented by the virtual image. In such augmented reality processing, the HMD 100 in this embodiment can determine a position of the virtual object taking into account an individual difference of eyes.

Note that the real object in this embodiment includes both of a "real object of interest" in which the user is interested (e.g., that the user looks at) and a "real background object", which is an object in which the user is not interested (e.g., that is in a visual field of the user but the user does not look at). The real object including both of the real object of interest and the real background object can be a processing target of the augmented reality processing of this embodiment.

The HMD 100 includes an image display unit 20 that causes the user to visually recognize the virtual image in a state in which the image display unit 20 is worn on the head of the user and a control unit (a controller) 10 that controls the image display unit 20. Note that, in the following explanation, the virtual image visually recognized by the user with the HMD 100 is referred to as "displayed image" as well for convenience. The HMD 100 emitting image light generated on the basis of image data is referred to as "display an image" as well.

A-1-1. Configuration of the Image Display Unit

Figure 2:
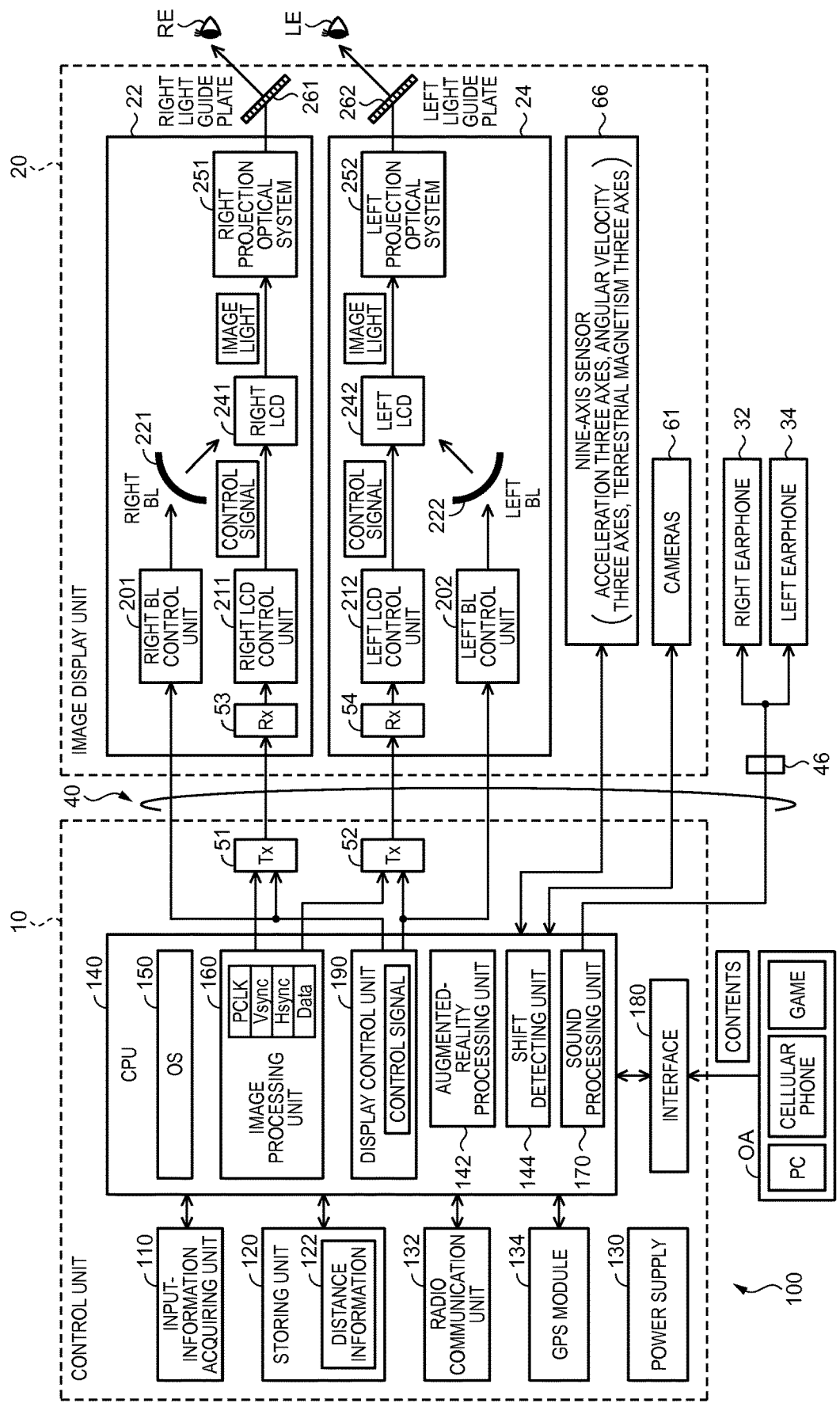
FIG. 2 is a block diagram functionally showing the configuration of an HMD.

FIG. 2 is a block diagram functionally showing the configuration of the HMD 100. The image display unit 20 is a wearing body worn on the head of the user. In this embodiment, the image display unit 20 has an eyeglass shape (FIG. 1). The image display unit 20 includes a right holding unit 21, a right display driving unit 22, a left holding unit 23, a left display driving unit 24, a right optical-image display unit 26, a left optical-image display unit 28, cameras 61, and a nine-axis sensor 66. Positional relations and functions of the units of the image display unit 20 in a state in which the user wears the image display unit 20 are explained.

As shown in FIG. 1, the right optical-image display unit 26 and the left optical-image display unit 28 are arranged to be respectively located in front of the right eye and in front of the left eye of the user. One end of the right optical-image display unit 26 and one end of the left optical-image display unit 28 are connected in a position corresponding to the middle of the forehead of the user. As shown in FIG. 2, the right optical-image display unit 26 includes a right light guide plate 261 and a dimming plate (not shown in the figure). The right guide plate 261 is formed of light-transmissive resin material or the like. The right light guide plate 261 guides image light output from the right display driving unit 22 to a right eye RE of the user while reflecting the image light along a predetermined optical path. The dimming plate is a thin plate-like optical device and is arranged to cover the front side (a side opposite to the side of the eyes of the user) of the image display unit 20. The dimming plate protects the right light guide plate 261 and suppresses, for example, damage and adhesion of stain to the right light guide plate 261. By adjusting the light transmittance of the dimming plate, it is possible to adjust an amount of external light made incident on the eyes of the user and adjust easiness of visual recognition of a virtual image. Note that the dimming plate can be omitted.

The left optical-image display unit 28 includes a left light guide plate 262 and a dimming plate (not shown in the figure). Details of the left light guide plate 262 and the dimming plate are the same as the right light guide plate 261 and the dimming plate of the right optical-image display unit 26. Note that the right optical-image display unit 26 and the left optical-image display unit 28 are collectively simply referred to as "optical-image display units" as well. The optical-image display units can adopt any system as long as the optical-image display units form a virtual image in front of the eyes of the user by using the image light. For example, the optical-image display units may be implemented using a diffraction grating or may be implemented using a transreflective film.

As shown in FIG. 1, the right holding unit 21 is provided to extend from the other end ER of the right optical-image display unit 26 to a position corresponding to the temporal region of the user. The left holding unit 23 is provided to extend from the other end EL of the left optical-image display unit 28 to a position corresponding to the temporal region of the user. The right holding unit 21 and the left holding unit 23 hold the image display unit 20 on the head of the user like temples of eyeglasses. Note that the right holding unit 21 and the left holding unit 23 are collectively simply referred to as "holding units" as well.

As shown in FIG. 1, the right display driving unit 22 is disposed on the inner side (a side opposed to the head of the user) of the right holding unit 21. The left display driving unit 24 is disposed on the inner side of the left holding unit 23. As shown in FIG. 2, the right display driving unit 22 includes a receiving unit (Rx) 53, a right backlight (BL) control unit 201 and a right backlight (BL) 221 functioning as a light source, a right LCD (Liquid Crystal Display) control unit 211 and a right LCD 241 functioning as a display device, and a right projection optical system 251. Note that the right backlight control unit 201, the right LCD control unit 211, the right backlight 221, and the right LCD 241 are collectively referred to as "image-light generating unit" as well.

The receiving unit 53 functions as a receiver for serial transmission between the control unit 10 and the image display unit 20. The right backlight control unit 201 drives the right backlight 221 on the basis of an input control signal. The right backlight 221 is a light emitting body such as an LED (Light Emitting Diode) or an electroluminescence (EL) device. The right LCD control unit 211 drives the right LCD 241 on the basis of a clock signal PCLK, a vertical synchronization signal VSync, a horizontal synchronization signal HSync, image data Data for the right eye input via the receiving unit 53. The right LCD 241 is a transmission liquid crystal panel on which a plurality of pixels are arranged in a matrix shape. The right projection optical system 251 is a collimate lens that changes image light emitted from the right LCD 241 to light beams in a parallel state.

The left display driving unit 24 includes a receiving unit (Rx) 54, a left backlight (BL) control unit 202 and a left backlight (BL) 222 functioning as a light source, a left LCD control unit 212 and a left LCD 242 functioning as a display device, and a left projection optical system 252. Details of these components are the same as the corresponding components of the right display driving unit 22. Note that the right display driving unit 22 and the left display driving unit 24 are correctively simply referred to as "display driving units" as well.

As shown in FIG. 1, the cameras 61 are stereo cameras respectively disposed in positions corresponding to upper parts of the outer corners of the left and right eyes of the user. The left and right cameras 61 respectively pick up images of an outside scene (a scene on the outside) in the visual field direction of the user in a state in which the HMD 100 is mounted and acquire two outside scene images corresponding to the left and the right. The cameras 61 are so-called visible light cameras. The outside scene images acquired by the cameras 61 are images representing the shape of an object from visible light radiated from the object. Note that the cameras 61 in this embodiment are stereo cameras but may be monocular cameras. Note that the cameras 61 function as an "external-image acquiring unit".

As shown in FIG. 1, the nine-axis sensor 66 is disposed in a position corresponding to the temple on the right side of the user. The nine-axis sensor 66 is a motion sensor that detects acceleration (three axes), angular velocity (three axes), and terrestrial magnetism (three axes). Since the nine-axis sensor 66 is provided in the image display unit 20, when the image display unit 20 is worn on the head of the user, the nine-axis sensor 66 functions as a motion detecting unit that detects the motion of the head of the user of the head mounted display 100. The motion of the head includes the speed, the acceleration, the angular velocity, the direction, and a change in the direction of the head.

As shown in FIG. 1, the image display unit 20 includes a connecting unit 40 for connecting the image display unit 20 to the control unit 10. The connecting unit 40 includes a main body cord 48 connected to the control unit 10, a right cord 42 and a left cord 44 branching from the main body cord 48, and a coupling member 46 provided at a branching point. A jack for connecting an earphone plug 30 is provided in the coupling member 46. A right earphone 32 and a left earphone 34 extend from the earphone plug 30. The image display unit 20 and the control unit 10 perform transmission of various signals via the connecting unit 40. As the cords of the connecting unit 40, for example, a metal cable and an optical fiber can be adopted.

A-1-2. Configuration of the Control Unit

The control unit 10 is a device for controlling the HMD 100. As shown in FIG. 1, the control unit 10 includes a determination key 11, a lighting unit 12, a display switching key 13, a track pad 14, a luminance switching key 15, a direction key 16, a menu key 17, and a power switch 18. The determination key 11 detects pressing operation and outputs a signal for determining content of the operation in the control unit 10. The lighting unit 12 is implemented by, for example, an LED and notifies, with a light emission state thereof, an operation state (e.g., ON/OFF of a light source) of the HMD 100. The display switching key 13 detects pressing operation and outputs, for example, a signal for switching a display mode of a content moving image to 3D and 2D.

The track pad 14 detects operation by a finger of the user on an operation surface of the track pad 14 and outputs a signal corresponding to detected content. As the track pad 14, various types such as an electrostatic type, a pressure type, and an optical type can be adopted. The luminance switching key 15 detects pressing operation and outputs a signal for increasing or reducing the luminance of the image display unit 20. The direction key 16 detects pressing operation on keys corresponding to the up, down, left, and right directions and outputs a signal corresponding to detected contents. The power switch 18 detects slide operation of the switch to switch a power supply state of the HMD 100.

As shown in FIG. 2, the control unit 10 includes an input-information acquiring unit 110, a storing unit 120, a power supply 130, a radio communication unit 132, a GPS module 134, a CPU 140, an interface 180, and transmitting units (Tx) 51 and 52. The units are connected to one another by a not-shown bus.

The input-information acquiring unit 110 acquires signals corresponding to operation input to the determination key 11, the display switching key 13, the track pad 14, the luminance switching key 15, the direction key 16, the menu key 17, and the power switch 18. Note that the input-information acquiring unit 110 can acquire operation inputs by various methods other than the operation inputs explained above. For example, the input-information acquiring unit 110 may acquire an operation input by a foot switch (a switch operated by the foot of the user). For example, the input-information acquiring unit 110 may acquire a visual line of the user detected by a visual-line detecting unit (not shown in the figure) and an operation input by a command associated with the movement of the eyes. The command may be set to be capable of being added by the user. For example, a gesture of the user may be detected using the cameras 61. An operation input by a command associated with the gesture maybe acquired. In the gesture detection, a fingertip of the user, a ring worn on the hand of the user, a medical instrument held by the user, or the like can be used as a mark for motion detection. If the operation input by these methods can be acquired, even in work in which it is difficult for the user to release the hands, the input-information acquiring unit 110 can acquire the operation input from the user.

The storing unit 120 is configured by a ROM, a RAM, a DRAM, a hard disk, or the like. Various computer programs such as an operating system (OS) are stored in the storing unit 120. In the storing unit 120, distance information 122 is stored.

In the distance information 122, information concerning distances concerning the eyes of the user to be used in correction processing explained below is stored in advance. In this embodiment, the distance information 122 includes an interocular distance and a display unit distance. The interocular distance is the distance between the right eye RE and the left eye LE of the user. In this embodiment, the distance between the center of the right optical-image display unit 26 and the center of the left optical-image display unit 28 is regarded as the distance between the right eye RE and the left eye LE of the user. Therefore, in the interocular distance, the distance (e.g., 65 mm) between the center of the right optical-image display unit 26 and the center of the left optical-image display unit 28 based on a design value of the HMD 100 is stored in advance. The display unit distance is the distance between the central pit of the right eye RE (or the left eye LE) of the user and the optical-image display unit. In this embodiment, a predetermined value (e.g., 45 mm) as a default value is stored in advance. The central pit is a name of a tissue located in the center of the macular area of the retinal of the human eye. The tissue contributes to the visual sense in a high accuracy central visual field. Note that the interocular distance and the display unit distance may be capable of being changed by the user as appropriate.

The power supply 130 supplies electric power to the units of the HMD 100. As the power supply 130, for example, a secondary cell can be used.

The radio communication unit 132 performs radio communication with an external apparatus according to a predetermined radio communication standard. The predetermined radio communication standard is, for example, short distance radio communication exemplified by an infrared ray and a Bluetooth (registered trademark) or a wireless LAN exemplified by IEEE802.11.

The GPS module 134 receives a signal from a GPS satellite to thereby detect the present position of the user of the HMD 100 and generates present position information representing present position information of the user. The present position information can be implemented by, for example, coordinates representing latitude and longitude.

The CPU 140 reads out and executes a computer program stored in the storing unit 120 to thereby function as an augmented-reality processing unit 142, a shift detecting unit 144, an operating system (OS) 150, an image processing unit 160, a sound processing unit 170, and a display control unit 190.

The augmented-reality processing unit 142 executes augmented reality processing. The augmented reality processing is processing for adding a virtual object to a real object actually present in a real world and displaying the virtual object. The augmented reality processing includes procedures a1 to a6 explained below.

(a1) The augmented-reality processing unit 142 acquires an outside scene image picked up by the cameras 61.

(a2) The augmented-reality processing unit 142 specifies a real object set as a target of addition of a virtual object (hereinafter referred to as "target object" as well) out of real objects included in the outside scene image acquired in the procedure a1.

(a3) The augmented-reality processing unit 142 acquires the position of the target object. The "position" includes a distance from the user and positions in the horizontal direction and the vertical direction in the visual field of the user. In acquiring the position of the target object, the augmented-reality processing unit 142 may calculate the position of the target object using two or more outside scene images acquired by the cameras 61, which are stereo cameras. The augmented-reality processing unit 142 may calculate the position of the target object concurrently using one or more outside scene images acquired by the cameras 61 and not-shown various sensors (e.g., a depth sensor and a rang-finding sensor).

(a4) The augmented-reality processing unit 142 acquires or generates an image, characters, a graphic symbol, or the like (e.g., a pointer, a shortcut, a menu, a radio button, a selection button, or a soft keyboard) representing the virtual object. The augmented-reality processing unit 142 may store the virtual object in the storing unit 120 in advance or may acquire the virtual object from another apparatus connected to the HMD 100 via a network.

(a5) The augmented-reality processing unit 142 generates additional image data in which the virtual object in the procedure a4 is arranged according to the position of the target object acquired in the procedure a3 and a black color is arranged in other portions. In this alignment, the augmented-reality processing unit 142 may use a characteristic part (an edge, etc.) of the target object and use a mark such as a marker attached to the target object. In the alignment, the augmented-reality processing unit 142 may use image recognition in which a model (or an image) of the target object stored in the storing unit 120 in advance is used. In the alignment, the augmented-reality processing unit 142 may perform the alignment on the basis of an instruction by the user. When arranging the virtual object, the augmented-reality processing unit 142 may apply image processing such as enlargement, reduction, rotation, or color conversion to the virtual object.

(a6) The augmented-reality processing unit 142 cooperates with the shift detecting unit 144 to execute "shift correction processing" explained below. According to the shift correction processing, the position of the virtual object in the additional image data is corrected taking into account the individual difference of the eyes and a final position of the virtual object is determined. Details of the shift correction processing are explained below.

The shift detecting unit 144 detects the individual difference of the eyes in the shift correction processing.

The image processing unit 160 performs signal processing for image display. Specifically, when contents (a video) are input via the interface 180 or the radio communication unit 132, the image processing unit 160 generates the imaged data Data based on the contents. When receiving image data from another functional unit of the HMD 100, the image processing unit 160 sets the received image data as the image data Data. Note that the image processing unit 160 may executes, on the image data Data, image processing such as resolution conversion processing, various kinds of tone correction processing such as adjustment of luminance and chroma, and keystone correction processing. The image processing unit 160 transmits the image data Data, the clock signal PCLK, the vertical synchronization signal VSync, and the horizontal synchronization signal HSync to the image display unit 20 via the transmitting units 51 and 52. Note that the image data Data transmitted via the transmitting unit 51 is referred to as "image data for right eye Data1" as well. The image data Data transmitted via the transmitting unit 52 is referred to as "image data for left eye Data2" as well.

The display control unit 190 generates control signals for controlling the right display driving unit 22 and the left display driving unit 24. Specifically, the display control unit 190 individually controls, using the control signals, ON/OFF of driving of the left and right LCDs 241 and 242 by the left and right LCD control units 211 and 212 and ON/OFF of driving of the left and right backlights 221 and 222 by the left and right backlight control units 201 and 202 to thereby control generation and emission of image lights by the right display driving unit 22 and the left display driving unit 24. The display control unit 190 transmits the control signals to the image display unit 20 via the transmitting units 51 and 52.

The sound processing unit 170 acquires a sound signal included in the contents, amplifies the acquired sound signal, and supplies the amplified sound signal to a not-shown speaker of the right earphone 32 and a not-shown speaker of the left earphone 34.

The interface 180 performs communication with an external apparatus OA according to a predetermined wired communication standard. The predetermined wired communication standard is, for example, Micro USB (Universal Serial Bus), USB, HDMI (High Definition Multimedia Interface; HDMI is a registered trademark), DVI (Digital Visual Interface), VGA (Video Graphics Array), composite, RS-232C (Recommended Standard 232), or wired LAN exemplified by IEEE802.3 As the external apparatus OA, for example, a personal computer PC, a cellular phone terminal, and a game terminal can be used.

Figure 3A:
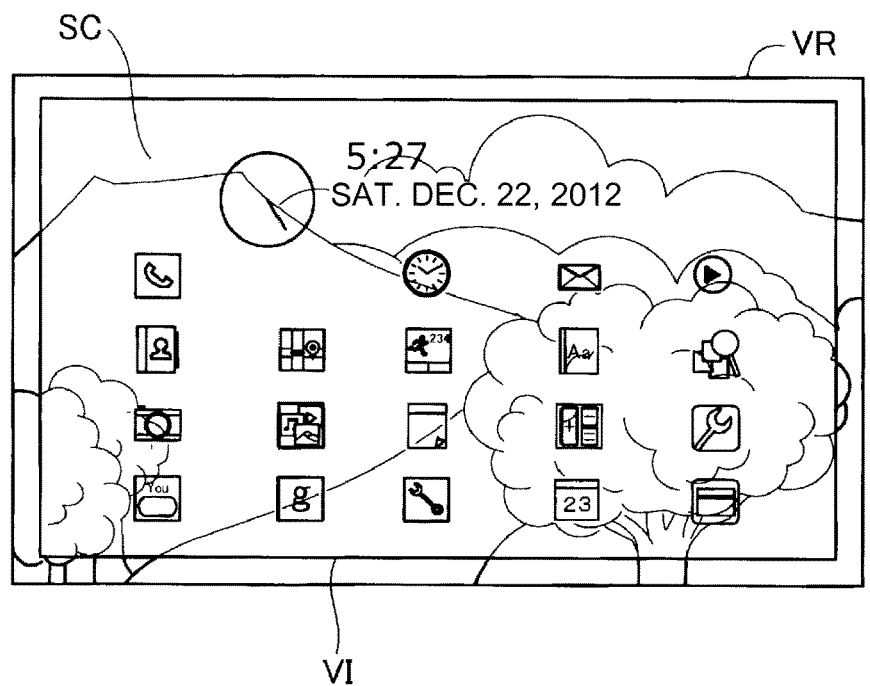
FIGS. 3A and 3B are explanatory diagrams showing examples of virtual images visually recognized by a user.
Figure 3B:
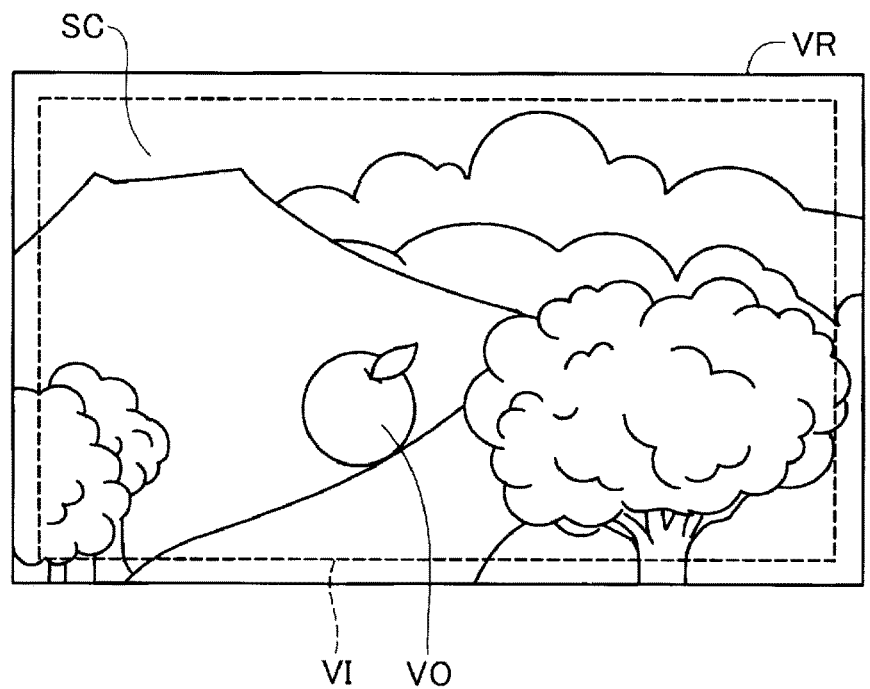

FIGS. 3A and 3B are explanatory diagrams showing examples of virtual images visually recognized by the user. FIG. 3A illustrates a visual field VR of the user obtained when the augmented reality processing is not executed. As explained above, the image lights guided to both the eyes of the user of the HMD 100 are focused on the retinas of the user, whereby the user visually recognizes a virtual image VI. In the example shown in FIG. 3A, the virtual image VI is a standby screen of the OS 150 of the HMD 100. The user visually recognizes an outside scene SC transmitted through the right optical-image display unit 26 and the left optical-image display unit 28. In this way, in a portion where the virtual image VI is displayed in the visual field VR, the user of the HMD 100 in this embodiment can view the virtual image VI and the outside scene SC behind the virtual image VI. In a portion where the virtual image VI is not displayed in the visual field VR, the user can directly view the outside scene SC through the optical-image display units.

FIG. 3B illustrates the visual field VR of the user obtained when the augmented reality processing is executed. By executing the augmented reality processing, the user visually recognizes the virtual image VI including a virtual object VO. The virtual object VO is an image of an apple arranged to overlap the foot of a mountain in the outside scene SC. In this way, the user can experience the augmented reality by viewing both of the virtual object VO included in the virtual image VI and a real object in the outside scene SC seen through behind the virtual image VI.

A-2. Shift Correction Processing

The shift correction processing is processing for correcting the position of the virtual object in the additional image data taking into account the individual difference of the eyes during the augmented reality processing. The shift correction processing is executed in the procedure a6 of the augmented reality processing as a subroutine of the augmented reality processing.

Figure 4:
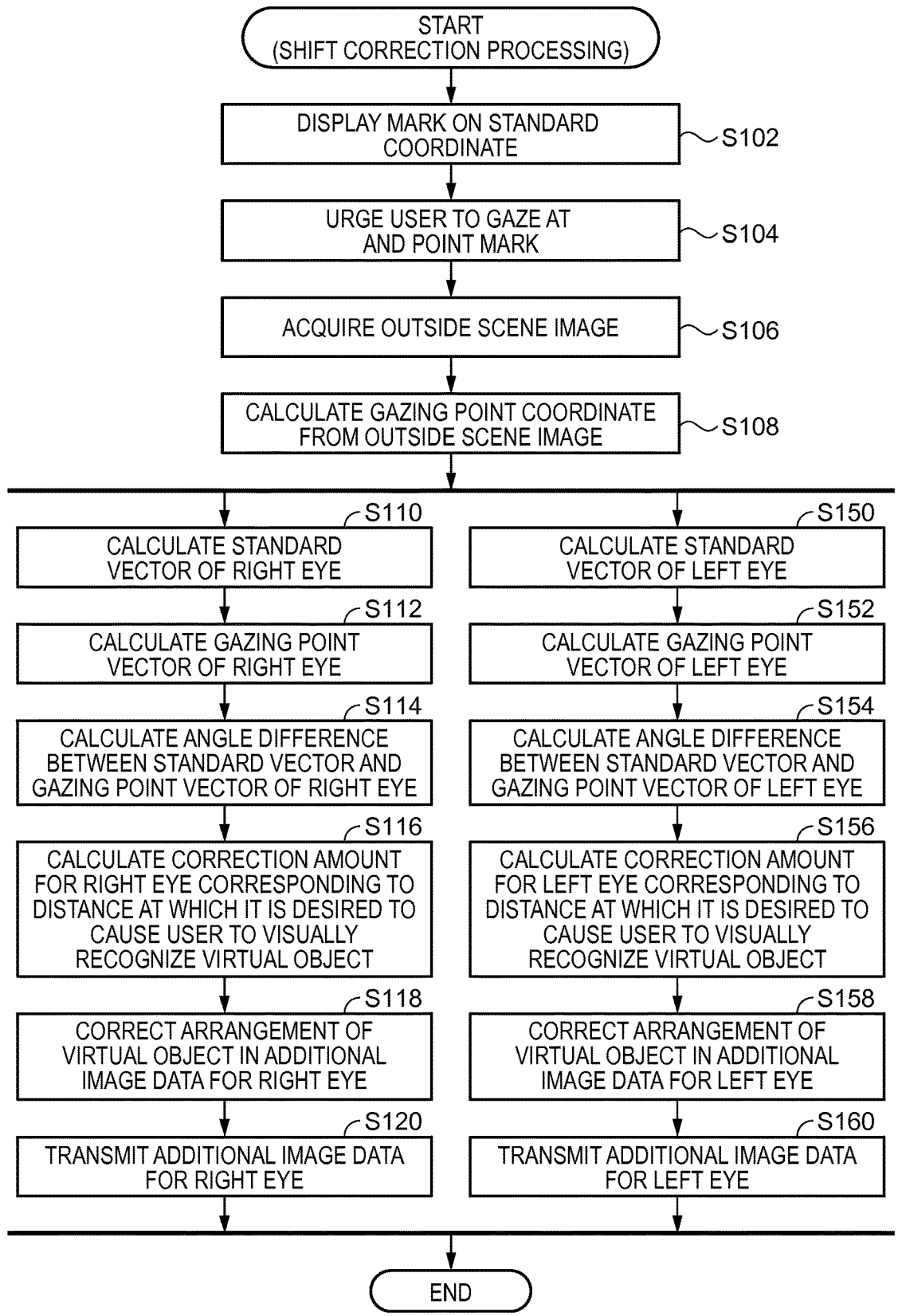
FIG. 4 is a flowchart for explaining a procedure of shift correction processing.
Figure 5:
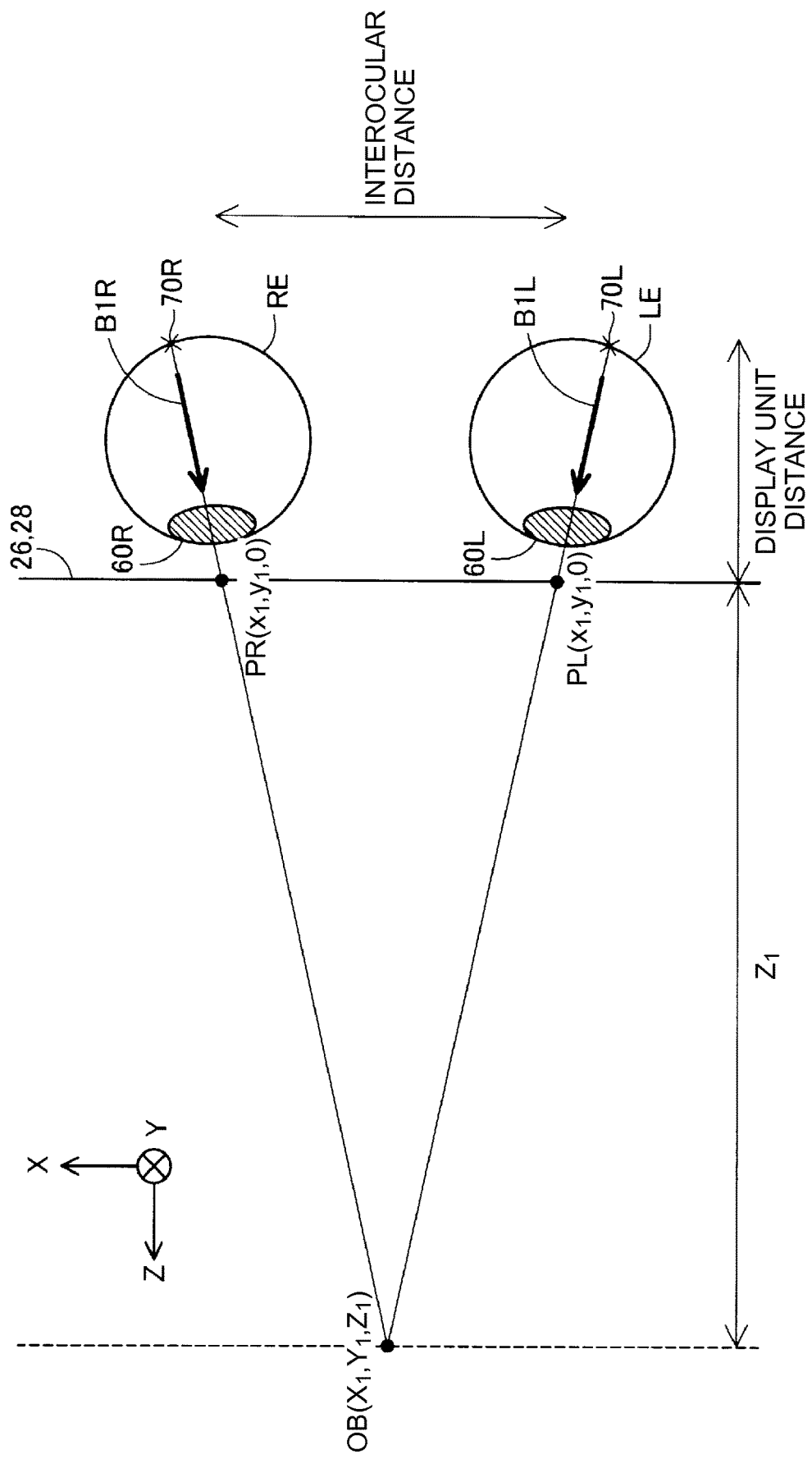
FIG. 5 is a diagram for explaining step S102 of the shift correction processing.

FIG. 4 is a flowchart for explaining a procedure of the shift correction processing. FIG. 5 is a diagram for explaining step S102 of the shift correction processing. In FIG. 5, for convenience of explanation, illustration is omitted concerning portions other than the right optical-image display unit 26 and the left optical-image display unit 28 of the HMD 100 and the right eye RE and the left eye LE of the user. The right eye RE includes a lens 60R and a central pit 70R. The left eye LE includes a lens 60L and a central pit 70L. In the following explanation, the right eye RE and the left eye LE are collectively referred to as "both the eyes" as well. Similarly, the lens 60R and the lens 60L are collectively referred to as "lenses" as well. The central pit 70R and the central pit 70L are collectively referred to as "central pits" as well. The right optical-image display unit 26 and the left optical-image display unit 28 are collectively referred to as "optical image display units" as well.

In step S102 of the shift correction processing (FIG. 4), the shift detecting unit 144 displays a virtual object OB functioning as a mark (hereinafter simply referred to as "mark OB" as well) on a standard coordinate. Specifically, when the mark OB is focused on both the eyes of a standard user, the shift detecting unit 144 generates the image data for right eye Data1 and the image data for left eye Data2 including the mark OB given with a parallax to cause the user to visually recognize the mark OB on a $(X_1, Y_1)$ coordinate a distance $Z_1$ ahead, in other words, on a standard coordinate $(X_1, Y_1, Z_1)$ on a three-dimensional space and transmits the image data for right eye Data1 and the image data for left eye Data2 to the image processing unit 160. In this case, a coordinate of the mark OB in the image data for right eye Data1 is represented as $PR(x_1, y_1, 0)$ and a coordinate of the mark OB in the image data for left eye Data2 is represented as $PL(x_1, y_1, 0)$. Note that PR and PL are different coordinate systems. In the following explanation, a value of $x_1$ of PR is described as "$PRx_1$", a value of $y_1$ is described as "$PRy_1$", and a value of $z_1$ is described as "$PRz_1$". The same applies to RL.

A relation among the standard coordinate $(X_1, Y_1, Z_1)$, $PR(x_1, y_1, 0)$, and $PL(x_1, y_1, 0)$ can be defined as described below.

$X_1 = PRx_1$ or $PLx_1$ $Y_1 = PRy_1$ or $PLy_1$ $Z_1$=Any point targeted by the parallax of the mark OB in the image data for right eye Data1 and the image data for left eye Data2. This point is a point at a distance shorter than the arm of the user.

In the above explanation, to simplify the explanation, a difference between $PRx_1$ and $PLx_1$ is neglected in $X_1$. When the standard coordinate $X_1$ is more strictly defined, the standard coordinate $X_1$ may be defined as described below. Note that, as the interocular distance and the display unit distance, values stored in the distance information 122 in advance are used.

$$X_1 - (\text{interocular distance}/2) \times \{\text{display unit distance}/(Z_1 + \text{display unit distance})\} = PRx_1$$

-continued $$X_1 + (\text{interocular distance}/2) \times \{\text{display unit distance}/(Z_1 + \text{display unit distance})\} = PLx_1$$

Figure 6:
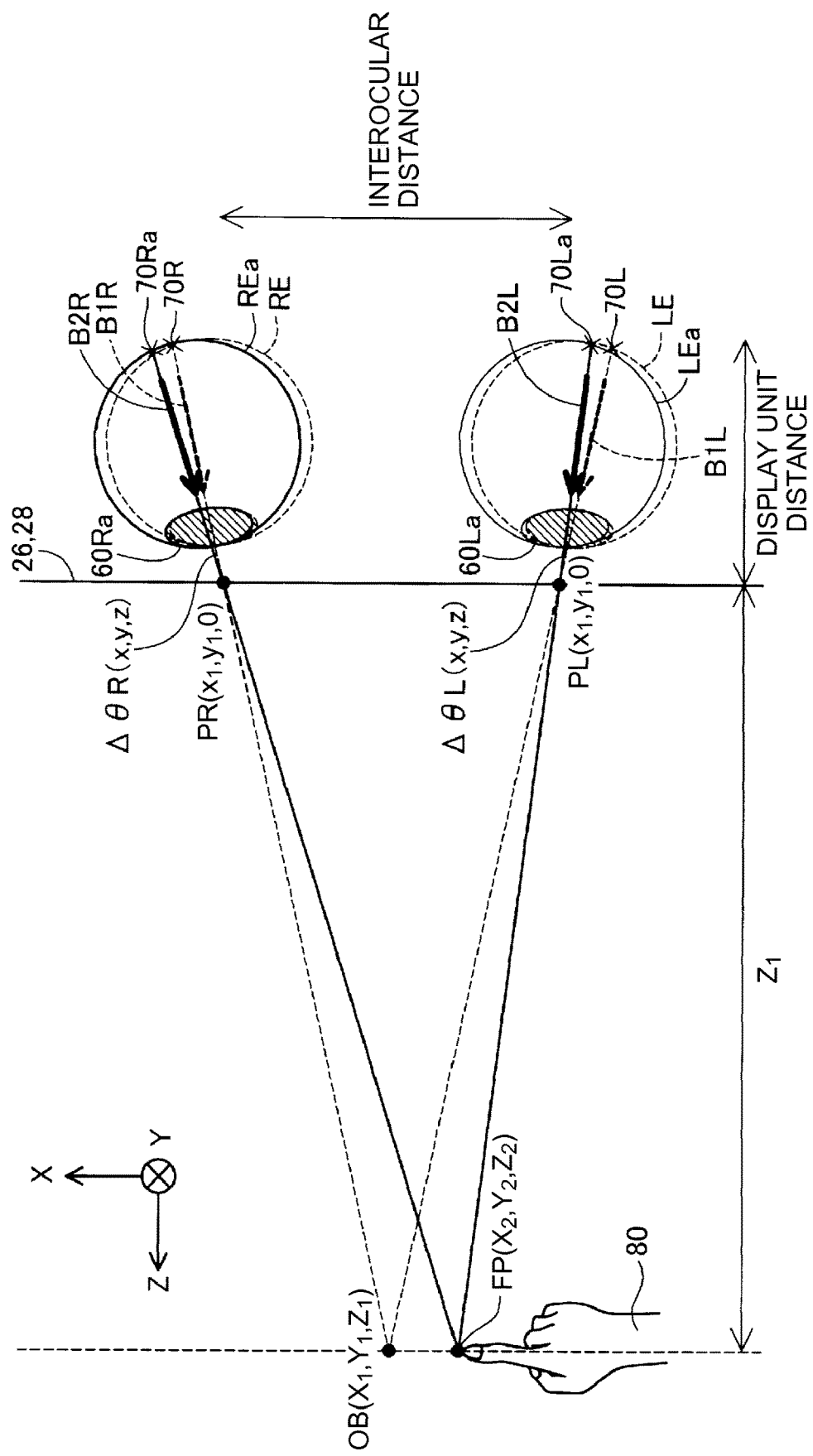
FIG. 6 is a diagram for explaining processing in step S104 and subsequent steps of the shift correction processing.

FIG. 6 is a diagram for explaining processing in step S104 and subsequent steps of the shift correction processing. In FIG. 6 as well, illustration of the portions other than the optical-image display units and both the eyes of the user is omitted. In FIG. 6, both the eyes RE and LE of the standard user shown in FIG. 5 are indicated by broken lines. Both eyes REa and LEa of an actual user during the execution of the shift correction processing are indicated by solid lines. Compared with the right eye RE and the left eye LE of the standard user, the right eye REa and the left eye LEa of the actual user are different in the shape of eyeballs, the positions of a lens 60Ra and a lens 60La, and the positions of a central pit 70Ra and a central pit 70La.

In step S104 in FIG. 4, the shift detecting unit 144 urges the actual user of the HMD 100 to point the mark OB displayed in step S102 while gazing at the mark OB. The shift detecting unit 144 may implement guidance by displaying a message for urging the gazing and the pointing as a virtual image or may implement the guidance using sound.

The actual user points, according to the guidance, the mark OB displayed in step S102. The shape of the eyes and the positions of the lenses and the central pits of the actual user are different from those of the standard user. Therefore, a point FP that the actual user recognizes as "the mark OB is present" and gazes at while pointing using a hand 80 (hereinafter referred to as "gazing point FP" as well) is different from the position of the mark OB as shown in FIG. 6. In the following explanation, a coordinate $(X_2, Y_2, Z_2)$ of the gazing point FP on the three-dimensional space is referred to as "gazing point coordinate" as well.

Figure 7:
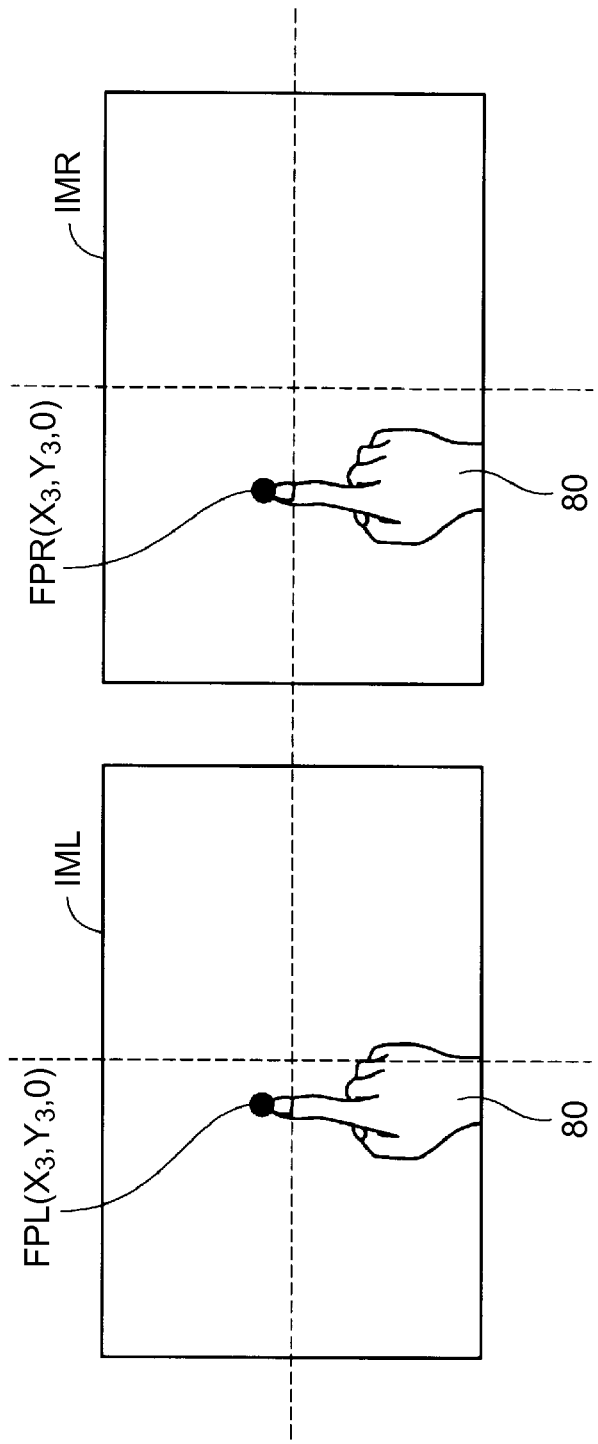
FIG. 7 is a diagram for explaining step S106 of the shift correction processing.

FIG. 7 is a diagram for explaining step S106 of the shift correction processing. In step S106 in FIG. 4, the shift detecting unit 144 acquires, with the cameras 61, which are the stereo cameras, an outside scene image IMR corresponding to the right eye RE of the actual user and an outside scene image IML corresponding to the left eye LE.

In step S108 in FIG. 4, the shift detecting unit 144 calculates the gazing point coordinate $(X_2, Y_2, Z_2)$ from the two outside scene images. Specifically, first, the shift detecting unit 144 calculates a coordinate (in other words, a coordinate of the gazing point) FPR $(x_3, y_3, 0)$ of a fingertip in the outside scene image IMR and a coordinate FPL $(x_3, y_3, 0)$ of the fingertip in the outside scene image IML. The FPR and the FPL are different coordinate systems. Note that, in the following explanation, a value of $x_3$ of the FPR is described as "FPRx$_3$" and a value of $y_3$ is described as "FPRy$_3$". The same applies to the FRL.

The shift detecting unit 144 can calculate the gazing point coordinate $(X_2, Y_2, Z_2)$ as explained below using the calculated coordinates FPR $(x_3, y_3, 0)$ and FPL $(x_3, y_3, 0)$.

$X_2$: calculated by solving Expressions 1 and 2 below. Note that, as the interocular distance and the display unit distance, values stored in the distance information 122 in advance are used.

$$X_2-(\text{interocular distance}/2)\times\{\text{display unit distance}/(Z_1+\text{display unit distance})\}=FPRx_3 \quad \text{(Expression 1)}$$

$$X_2+(\text{interocular distance}/2)\times\{\text{display unit distance}/(Z_1+\text{display unit distance})\}=FPLx_3 \quad \text{(Expression 2)}$$

$Y_2$=FPRy$_3$ or FPLy$_3$ $Z_2$=a point calculated using a trigonometric function from a parallax (i.e., a difference between FPRx$_3$ and FPLx$_3$) and the interocular distance in the distance information 122.

According to step S108, the shift detecting unit 144 can calculate the gazing point coordinate $(X_2, Y_2, Z_2)$ using at least the two outside scene images IMR and IML acquired by the stereo cameras generally mounted on the head-mounted display device (the HMD 100).

Subsequent processing for the right eye (steps S110 to S120) and processing for the left eye (steps S150 to S160) in the shift correction processing (FIG. 4) are executed in parallel. In the following explanation, first, only the processing for the right eye is explained.

In step S110 in FIG. 4, the shift detecting unit 144 calculates a standard vector B1R of the right eye. Specifically, the shift detecting unit 144 calculates a vector connecting the coordinate PR$(x_1, y_1, 0)$ of the mark OB in the image data for right eye Data1 shown in FIG. 5 and the standard coordinate $(X_1, Y_1, Z_1)$ where the mark OB is assumed to be visually recognized by both the eyes of the standard user. The shift detecting unit 144 sets the calculated vector as the standard vector B1R of the right eye. The standard vector B1R of the right eye can be identified as a vector connecting the central pit 70R and the center of the lens 60R of the right eye RE of the standard user.

In step S112, the shift detecting unit 144 calculates a gazing point vector B2R of the right eye. Specifically, the shift detecting unit 144 calculates a vector connecting the coordinate PR$(x_1, y_1, 0)$ of the mark OB in the image data for right eye Data1 shown in FIG. 6 and the gazing point coordinate $(X_2, Y_2, Z_2)$ where the mark OB is visually recognized by both the eyes of the actual user. The shift detecting unit 144 sets the calculated vector as the gazing point vector B2R of the right eye. The gazing point vector B2R of the right eye can be identified as a vector connecting the central pit 70Ra and the center of the lens 60Ra of the right eye REa of the actual user.

In step S114, the shift detecting unit 144 calculates an angle difference $\Delta\theta R(x, y, z)$ between the standard vector B1R of the right eye and the gazing point vector B2R of the right eye. In the angle difference $\Delta\theta R(x, y, z)$, x represents an angle difference of a pitch angle, y represents an angle difference of a yaw angle, and z represents an angle difference of a roll angle.

Figure 8:
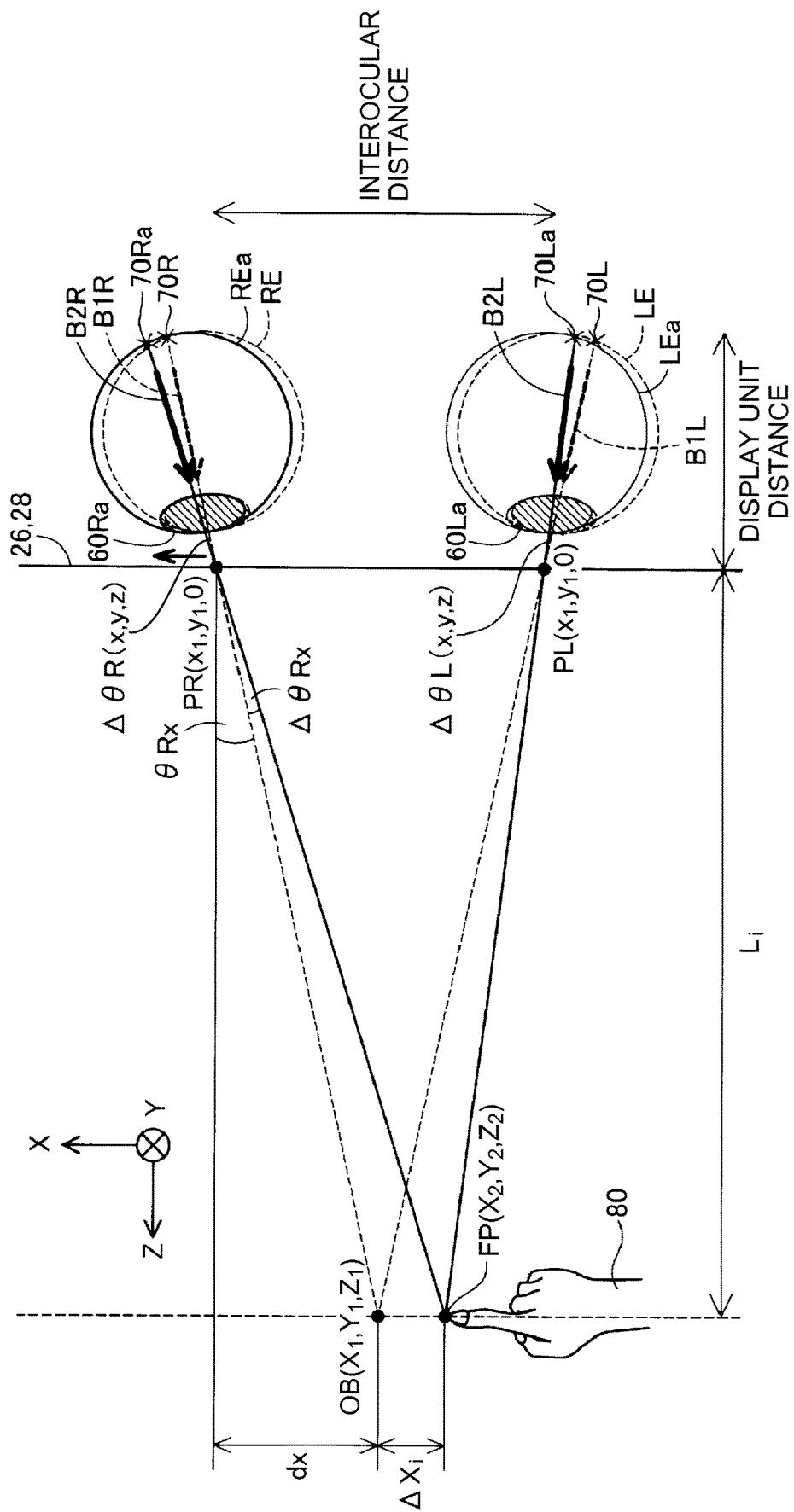
FIG. 8 is a diagram for explaining processing in step S116 and subsequent steps of the shift correction processing.

FIG. 8 is a diagram for explaining processing in step S116 and subsequent steps of the shift correction processing. In FIG. 8 as well, illustration of the portions other than the optical-image display units and both the eyes of the user is omitted. Both the eyes RE and LE of the standard user are indicated by broken lines and both the eyes REa and LEa of the actual user are indicated by solid lines. A distance $L_0$ shown in FIG. 8 is the display unit distance stored in the distance information 122.

In step S116 in FIG. 4, the augmented-reality processing unit 142 calculates a correction amount for right eye corresponding to a distance $L_i$ (FIG. 8) at which it is desired to cause the actual user to visually recognize the virtual object. Specifically, an angle difference of a pitch angle between an imaginary straight line imaginarily drawn from the right eye RE of the user in an infinity direction and the standard vector B1R of the right eye is represented as $\theta Rx$. An angle difference of a pitch angle in the angle difference $\Delta\theta R(x, y, z)$ between the standard vector B1R of the right eye and the gazing point vector B2R of the right eye is represented as $\Delta\theta Rx$. Length in the x-axis direction between the imaginary straight line imaginarily drawn from the right eye RE of the user in the infinity direction and the standard coordinate $(X_1,$ $Y_1$, $Z_1$) is represented as dx. Length in the x-axis direction between the standard coordinate ($X_1$, $Y_1$, $Z_1$) and the gazing point coordinate ($X_2$, $Y_2$, and $Z_2$) is represented as $\Delta X_i$.

In this case, the values described above satisfy a relation of the following Expressions 3 and 4:

$$\tan \theta Rx = dx/L_i \quad \text{(Expression 3)}$$

$$\tan(\theta Rx + \Delta \theta Rx) = (dx + \Delta X_i)/L_i \quad \text{(Expression 4)}$$

The augmented-reality processing unit 142 can calculate the correction amount for right eye in the x-axis direction of the coordinate $PR(x_1, y_1, 0)$ of the mark OB in the image data for right eye Data1 by solving Expressions 3 and 4 for "$\Delta \theta Rx$".

Similarly, the augmented-reality processing unit 142 calculates correction amounts for right eye in the y-axis direction and the z-axis direction of the coordinate $PR(x_1, Y_1, 0)$ of the mark OB in the image data for right eye Data1. For example, when the correction amount in the y-axis direction is calculated, in the above description, "pitch angle", "x-axis direction", "$\theta Rx$", "$\Delta \theta Rx$", "dx", and "$\Delta X_1$" only have to respectively read "yaw angle", "y-axis direction", "$\theta Ry$", "$\Delta \theta Ry$", "dy", and "$\Delta y_1$".

In step S118 in FIG. 4, the augmented-reality processing unit 142 corrects, on the basis of the correction amounts for right eye in the x, y, and z-axis directions calculated in step S116, the position of the virtual object in the additional image data generated in the procedure a5 of the augmented reality processing.

In step S120, the augmented-reality processing unit 142 transmits the additional image data after the correction to the image processing unit 160 as the image data for right eye Data1.

In steps S150 to S160 in FIG. 4, processing for the left eye is executed. That is, the shift detecting unit 144 calculates a standard vector B1L of the left eye (step S150), calculates a gazing point vector B2L of the left eye (step S152), and calculates an angle difference $\Delta \theta L(x, y, z)$ between the standard vector B1L and the gazing point vector B2L (step S154). The augmented-reality processing unit 142 calculates a correction amount for left eye corresponding to the calculated angle difference $\Delta \theta L(x, y, z)$ and the distance $L_i$ at which it is desired to cause the actual user to visually recognize the virtual object (step S156). The augmented-reality processing unit 142 transmits the additional image data, in which the position of the virtual object is corrected using the correction amount for left eye (step S158), to the image processing unit 160 as the image data for left eye Data2 (step S160).

In the image processing unit 160 that receives the image data for right eye Data1 and the image data for left eye Data2, the display processing explained above is performed. As a result, image light guided to the right eye REa and image light guided to the left eye LEa are focused on the retinas (in particular, in the vicinities of the central pits), whereby the actual user of the HMD 100 can visually recognize a virtual image including the virtual object aligned taking into account the individual difference of the human eyes (differences in the positions of the eyes, the shape of the eyeballs, and the positions of the parts related to a visual sense in the eyes (e.g., the lenses, the retinas, and the central pits)).

As explained above, according to the shift correction processing (FIG. 4) in this embodiment, the shift detecting unit 144 can detect a shift between the standard coordinate ($X_1$, $Y_1$, $Z_1$) of the mark OB formed on the three-dimensional space and the gazing point coordinate ($X_2$, $Y_2$, $Z_2$) representing the gazing point of the user gazing at the mark OB. This "shift" is a shift between a gazing point FP of the standard user gazing at the mark OB and the gazing point FP of the actual user of the head-mounted display device (the HMD 100) gazing at the mark OB and is a shift caused by the individual difference of the eyes REa and LEa of the actual user. The augmented-reality processing unit 142 arranges, using the shift between the standard coordinate ($X_1$, $Y_1$, $Z_1$) and the gazing point coordinate ($X_2$, $Y_2$, $Z_2$) (i.e., the shift caused by the individual difference of the eyes REa and LEa of the actual user) detected by the shift detecting unit 144, the virtual object to be displayed additionally to the real object (a procedure a6). As a result, it is possible to provide the head-mounted display device capable of implementing the augmented reality processing (the procedures a1 to a6) that takes into account the individual difference of the eyes.

Further, according to the shift correction processing (FIG. 4) in this embodiment, the shift detecting unit 144 can define the shift between the standard coordinate ($X_1$, $Y_1$, $Z_1$) and the gazing point coordinate ($X_2$, $Y_2$, $Z_2$) as the angle differences $\Delta \theta R$ and $\Delta \theta L$ between the "standard vectors B1R and B1L", which can be identified as vectors connecting the central pits 70R and 70L and the centers of the lenses 60R and 60L of the eyes RE and LE of the standard user, and the "gazing point vectors B2R and B2L", which can be identified as vectors connecting the central pits 70Ra and 70La and the centers of the lenses 60Ra and 60La of the eyes REa and LEa of the actual user. The angle differences $\Delta \theta R$ and $\Delta \theta L$ include the angle differences $\Delta \theta Rx$ and $\Delta \theta Lx$ of the pitch angle, the angle differences $\Delta \theta Ry$ and $\Delta \theta Ly$ of the yaw angle, and the angle differences $\Delta \theta Rz$ and $\Delta \theta Lz$ of the roll angle. Therefore, the shift detecting unit 144 can calculate angle differences between the standard vectors B1R and B1L and the gazing point vectors B2R and B2L concerning each of the x axis, the y axis, and the z axis in the rectangular coordinate system on the three-dimensional space.

A-3. Variations of the Shift Correction Processing

Note that variations 1 to 3 explained below may be applied to the shift correction processing (FIG. 4). The variations 1 to 3 maybe independently adopted or maybe adopted in combination. Note that in explanation of the variations 1 to 3, only differences from the embodiment are explained. Steps not explained below are the same as the steps in the embodiment.

A-3-1. Variation 1

In the variation 1, a shift between a standard coordinate and a gazing point coordinate is detected concerning a different plurality of standard coordinates to improve accuracy of the shift correction processing.

In FIG. 4, the shift detecting unit 144 repeatedly executes, while changing specific values of $X_1$, $Y_1$, and $Z_1$ of the standard coordinate, the series of processing in steps S102 to S114, that is, the series of processing for causing the user to visually recognize the mark OB on the standard coordinate ($X_1$, $Y_1$, $Z_1$), calculating the gazing point coordinate ($X_2$, $Y_2$, $Z_2$), and detecting the angle difference $\Delta \theta R(x, y, z)$ between the standard vector B1R and the gazing point vector B2R as the shift between the standard coordinate and the gazing point coordinate. Similarly, the shift detecting unit 144 repeatedly executes the series of processing in steps S102 to S154 while changing the specific values of $X_1$, $Y_1$, and $Z_1$ of the standard coordinate.

In this case, the standard coordinate is preferably distributed as much as possible within the visual field of the user. For example, the shift detecting unit 144 preferably sets the standard coordinate in first processing at the right upper end portion of the visual field of the user, sets the standard coordinate in second processing at the upper left end portion of the visual field of the user, sets the standard coordinate in third processing at the lower left end portion of the visual field of the user, sets the standard coordinate in fourth processing at the lower right end portion of the visual field of the user, and sets the standard coordinate in fifth processing in the center of the visual field of the user.

In step S116 in FIG. 4, the augmented-reality processing unit 142 calculates the correction amount for right eye using a calculated plurality of shifts (angle differences $\Delta\theta R$) between the standard coordinates and the gazing point coordinates. Specifically, the augmented-reality processing unit 142 can calculate the correction amount for right eye using one of methods b1 and b2 explained below.

(b1) The augmented-reality processing unit 142 selects, out of the calculated plurality of angle differences $\Delta\theta R$, one angle difference $\Delta\theta R$ calculated using the standard coordinate closest to a position in the x-axis direction and a direction in the y-axis direction where it is desired to cause the user to visually recognize the virtual object. The augmented-reality processing unit 142 executes the processing explained in step S116 in FIG. 4 using the selected angle difference $\Delta\theta R$ to calculate the correction amount for right eye.

(b2) The augmented-reality processing unit 142 calculates an average of the calculated plurality of angle differences $\Delta\theta R$. The augmented-reality processing unit 142 calculates the average for each of the angle difference $\Delta\theta Rx$ of the pitch angle, the angle difference $\Delta\theta Ry$ of the yaw angle, and the angle difference $\Delta\theta Rz$ of the roll angle. The augmented-reality processing unit 142 executes the processing explained in step S116 of FIG. 4 using the calculated average of the angle differences $\Delta\theta R$ to calculate the correction amount for right eye.

Similarly, in step S156, the augmented-reality processing unit 142 calculates the correction amount for left eye using the calculated plurality of angle differences $\Delta\theta L$.

As explained above, according to the variation 1, the augmented-reality processing unit 142 arranges the virtual object using the plurality of shifts ($\Delta\theta R$ and $\Delta\theta L$) respectively detected concerning the different plurality of standard coordinates ($X_1, Y_1, Z_1$). Therefore, it is possible to improve accuracy of the individual difference of the eyes taken into account in the augmented reality processing (the procedures a1 to a6).

A-3-2. Variation 2

In a variation 2, as in the variation 1, shifts between standard coordinates and gazing point coordinates are detected concerning a different plurality of standard coordinates to improve accuracy of the shift correction processing. Further, in the variation 2, any indication formed by any application in the HMD 100 is used as the mark OB. Note that, in explanation of the variation 2, only differences from the variation 1 are explained. Steps not explained below are the same as the steps in the variation 1.

Figure 9A:
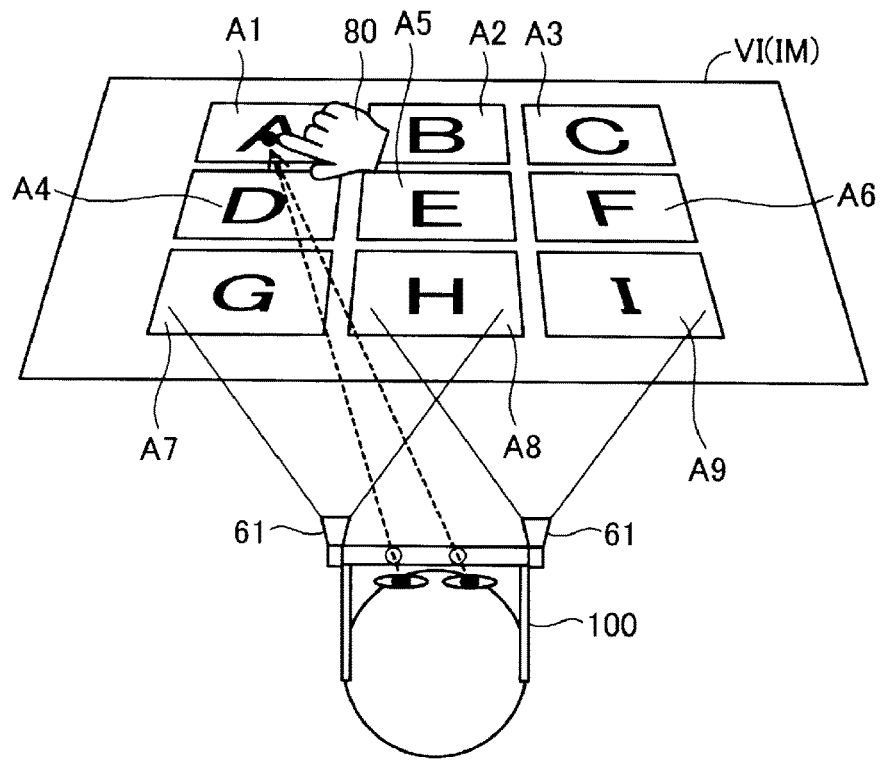
FIGS. 9A and 9B are diagrams for explaining a variation 2.
Figure 9B:
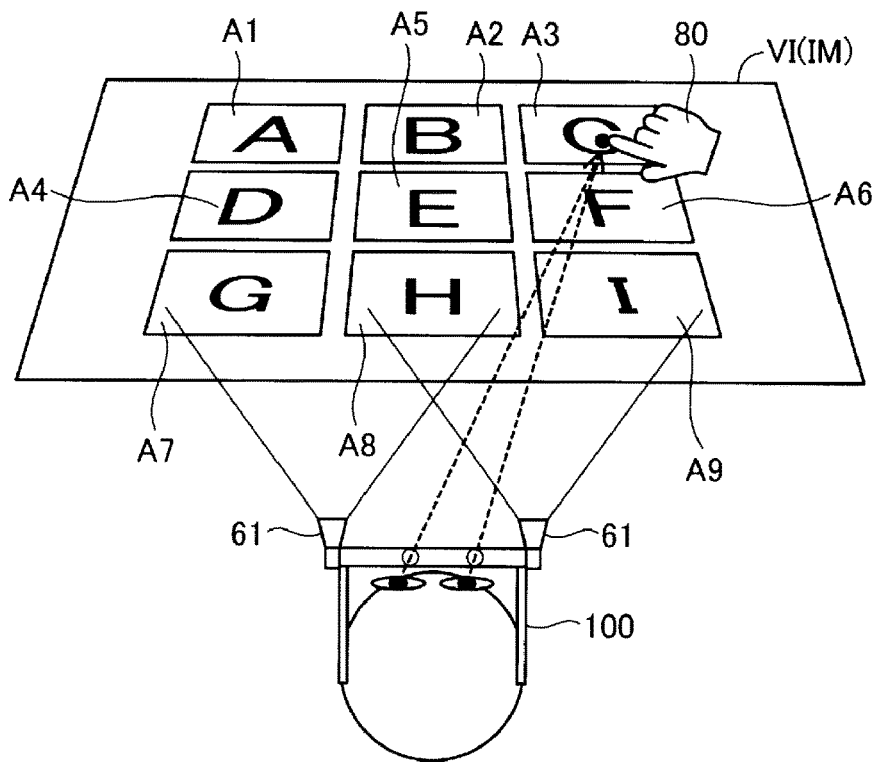

FIGS. 9A and 9B are diagrams for explaining the variation 2. Both of FIG. 9A and FIG. 9B schematically show the virtual image VI schematically representing an authentication screen IM formed by an authentication application in the HMD 100. The authentication screen IM includes nine input areas A1 to A9. The authentication application is an application that, when a password input by the user using input areas A1 to A9 and a password stored in the HMD 100 in advance coincide with each other, determines that the user is a legitimate user of the HMD 100 and executes processing such as screen unlock.

The shift detecting unit 144 sets the "standard coordinate" in the repetition of the series of processing in steps S102 to S114 (in the case of the left eye, steps S102 to S154) to a coordinate where a touch of the user is assumed in the authentication screen IM. For example, when the password of the user is "ACH", the shift detecting unit 144 sets the standard coordinate in first processing to, for example, a coordinate of the center of the input area A1 allocated with a character string "A" (FIG. 9A). In this case, the indication "A" of the input area A1 is used as the mark OB in the first processing. Similarly, the shift detecting unit 144 sets the standard coordinate in second processing to a coordinate in the center of the input area A3 allocated with a character string "C" (FIG. 9B) and sets the standard coordinate in third processing to a coordinate in the center of the input area A8 allocated with a character string "H". In this case, the indication "C" of the input area A3 is used as the mark OB in the second processing and the indication "H" of the input area A8 is used as the mark OB in the third processing.

Note that, in the above explanation, the authentication application is illustrated. However, the shift detecting unit 144 can use, as the mark OB, any indication (e.g., a character, a figure, or an image) formed by any application (e.g., a game application, a character input application, or an input application by gesture) in the HMD 100.

As explained above, according to the variation 2, the shift detecting unit 144 can execute, using, as the mark OB, any indication formed by any application in the head-mounted display device (the HMD 100), the series of processing for detecting the shift ($\Delta\theta R$, $\Delta\theta L$) between the standard coordinate ($X_1, Y_1, Z_1$) and the gazing point coordinate ($X_2, Y_2, Z_2$). As a result, it is possible to reduce labor of the user.

A-3-3. Variation 3

In a variation 3, processing same as the processing in the embodiment is implemented without using the stereo cameras.

In the variation 3, the cameras 61 shown in FIG. 2 are monocular cameras. The image display unit 20 of the HMD 100 is mounted with a depth sensor that can acquire depths (distances) to points in the front. Note that the depth sensor functions as a "distance acquiring unit".

In step S106 in FIG. 4, the shift detecting unit 144 acquires an outside scene image in the visual field direction of the user using the cameras 61. Further, the shift detecting unit 144 acquires depths between the user and points in the visual field direction of the user using the depth sensor.

In step S108, the shift detecting unit 144 calculates the gazing point coordinate ($X_2, Y_2, Z_2$) using the outside scene image acquired by the cameras 61 and the depths acquired by the depth sensor. Specifically, the shift detecting unit 144 can calculate the gazing point coordinate ($X_2, Y_2, Z_2$) as described below using a coordinate ($x_4, y_4$) of a fingertip in the outside scene image.

$X_2 = x_4$ $Y_2 = y_4$ $Z_2 =$ The depths (distances) acquired by the depth sensor Note that, in the above explanation, the depth sensor is described as an example of the distance acquiring unit. However, a function of the distance acquiring unit may be substituted by other sensors such as an ultrasonic sensor and an infrared sensor.

As explained above, according to the variation 3, when the outside-scene-image acquiring unit (the cameras 61) can acquire only one outside scene image, the shift detecting unit 144 can calculate the gazing point coordinate ($X_2, Y_2, Z_2$) by concurrently using the distance (the depth) to the indication (the fingertip of the user) acquired by the distance acquiring unit (the depth sensor).

B. Modifications

In the embodiment, a part of the components implemented by hardware may be replaced with software. Conversely, a part of the components implemented by software may be replaced with hardware. Besides, modifications explained below are also possible.

Modification 1

In the embodiment, the configuration of the HMD is illustrated. However, the configuration of the HMD can be optionally set in a range not departing from the spirit of the invention. For example, addition, deletion, conversion, and the like of the components can be performed.

The allocation of the constituent elements to the control unit and the image display unit is only an example. Various forms of the allocation can be adopted. For example, forms explained below may be adopted.

(i) A form in which processing functions such as a CPU and a memory are mounted on the control unit and only a display function is mounted on the image display unit (ii) A form in which the processing functions such as the CPU and the memory are mounted on both of the control unit and the image display unit (iii) A form in which the control unit and the image display unit are integrated (e.g., a form in which the control unit is included in the image display unit and functions as an eyeglass-type wearable computer)

(iv) A form in which a smart phone or a portable game machine is used instead of the control unit (v) A form in which the control unit and the image display unit are connected via a wireless signal transmission line such as a wireless LAN, infrared communication, or a Bluetooth (registered trademark) and a connecting unit (a cord) is removed. Note that, in this case, power supply to the control unit or the image display unit may be carried out wirelessly.

For example, the configurations of the control unit and the image display unit illustrated in the embodiment can be optionally changed. Specifically, for example, both of the transmitting unit (Tx) of the control unit and the receiving unit (Rx) of the image display unit may include a function capable of performing bidirectional communication and may function as a transmitting and receiving unit. For example, a part of the interface for operation (the keys, the track pad, etc.) included in the control unit may be omitted. Another interface for operation such as a stick for operation may be included in the control unit. For example, devices such as a keyboard and a mouse may be connectable to the control unit such that the control unit receives inputs from the keyboard and the mouse. For example, the secondary cell is used as the power supply. However, the power supply is not limited to the secondary cell. Various cells can be used. For example, a primary cell, a fuel cell, a solar cell, or a thermal cell may be used.

Figure 10A:
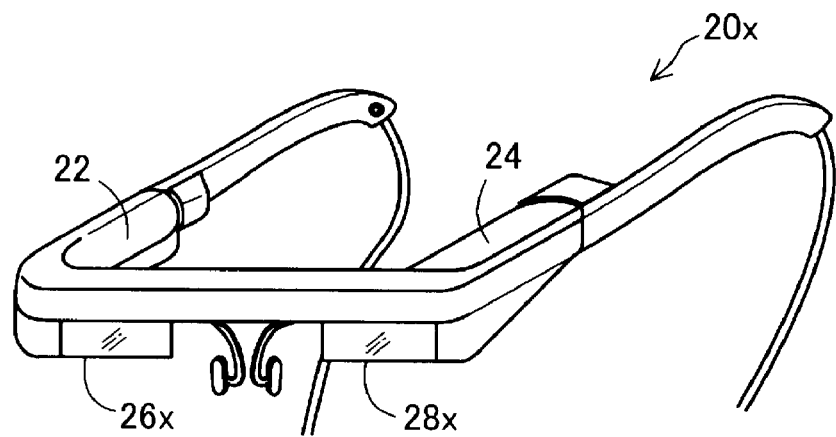
FIGS. 10A and 10B are explanatory diagrams showing the configurations of the exteriors of HMDs in a modification.
Figure 10B:
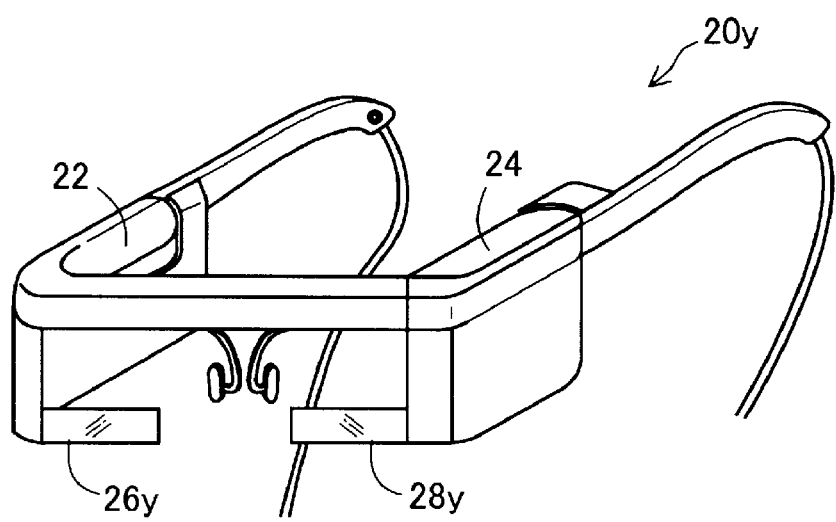

FIGS. 10A and 10B are explanatory diagrams showing the configurations of the exteriors of HMDs in a modification. An image display unit 20x shown in FIG. 10A includes a right optical-image display unit 26x and a left optical-image display unit 28x. The right optical-image display unit 26x and the left optical-image display unit 28x are formed smaller than the optical member in the embodiment and are respectively arranged obliquely above the right eye and the left eye of the user when the user wears the HMD. An image display unit 20y shown in FIG. 10B includes a right optical-image display unit 26y and a left optical-image display unit 28y. The right optical-image display unit 26y and the left optical-image display unit 28y are formed smaller than the optical member in the embodiment and are respectively arranged obliquely below the right eye and the left eye of the user when the user wears the HMD. In this way, the optical-image display units only have to be arranged in the vicinities of the eyes of the user. The size of optical members forming the optical-image display units also may be any size. The optical-image display units can also be implemented as an HMD of a form in which the optical-image display units cover only a portion of the eyes of the user, in other words, a form in which the optical-image display unit do not completely cover the eyes of the user.

For example, the processing units (e.g., the image processing unit, the display control unit, the augmented-reality processing unit) included in the control unit may be configured using an ASIC (Application Specific Integrated Circuit) designed for implementing the functions.

For example, the HMD is the transmissive HMD of a binocular type. However, the HMD may be a HMD of a monocular type. For example, the HMD may be configured as a nontransmissive HMD that blocks transmission of an outside scene in a state in which the user wears the HMD or may be configured as a video see-through device in which a camera is mounted on the nontransmissive HMD. For example, as the earphone, an ear hook type or a headband type may be adopted. The earphone may be omitted.

For example, instead of the image display unit worn like the eyeglasses, a normal flat display device (a liquid crystal display device, a plasma display device, an organic EL display device, or the like) may be adopted. In this case, the control unit and the image display unit may be connected by wire or by radio. Consequently, the control unit can also be used as a remote controller of the normal flat display device. For example, instead of the image display unit worn like the eyeglasses, image display units of other forms such as an image display unit worn like a hat and an image display unit incorporated in a body protector such as a helmet may be adopted. For example, the image display unit may be configured as a head-up display (HUD) mounted on vehicles such as an automobile and an airplane or other transportation means.

For example, the image-light generating unit may include components for implementing another system in addition to the components (the backlights, the backlight control units, the LCDs, and the LCD control units) or instead of the components. For example, the image-light generating unit may include an organic EL (organic Electro-Luminescence) display and an organic EL control unit. For example, the image generating unit can include a digital micro mirror device or the like instead of the LCD. For example, the invention can also be applied to a head-mounted display device of a laser retina projection type.

Modification 2

In the embodiment, the examples of the augmented reality processing and the shift correction processing are explained. However, the procedures of these kinds of processing explained in the embodiment are only examples. Various modifications of the procedures are possible. For example, a part of the steps maybe omitted or still other steps maybe added. The order of steps to be executed may be changed.

For example, step S104 of the shift correction processing (FIG. 4) may be omitted. In particular, as in the variation 2, when any indication formed by any application is used as the mark, since the user often knows "a place that the user should point", the guidance in step S104 is often unnecessary.

For example, steps S110 to S114 and steps S150 to S154 may be omitted. In this case, in step S116 and step S156, the augmented-reality processing unit can calculate the correction amount for right eye and the correction amount for left eye using the difference between the values of the standard coordinate ($X_1$, $Y_1$, $Z_1$) in step S102 and the gazing point coordinate ($X_2$, $Y_2$, $Z_2$) calculated in step S108.

For example, in the virtual image formed in front of the eyes of the user in the augmented reality processing, only the virtual object may be included or other information (e.g., a menu bar and a clock) other than the virtual object may be included.

Modification 3

The invention is not limited to the embodiments, the examples, and the modifications explained above and can be implemented as various configurations without departing from the spirit of the invention. For example, the technical features in the embodiments, the examples, and the modifications corresponding to the technical features in the forms described in the summary can be replaced or combined as appropriate in order to solve a part or all of the problems or attain a part or all of the effects. Unless the technical features are explained in this specification as essential technical features, the technical features can be deleted as appropriate.

The entire disclosure of Japanese Patent Application No. 2014-232750, filed Nov. 17, 2014 is expressly incorporated by reference herein.

What is claimed is:

1. A head-mounted display device with which a user can visually recognize a virtual image and an outside scene, the head-mounted display device comprising:
    an image display configured to display a virtual image having a plurality of marks; and
    a processor programmed to:
        display a first mark out of the plurality of marks at a predetermined first standard coordinate on the image display,
        calculate a first gazing point coordinate at which a user gazes at the first mark after displaying of the first mark based on the user's hand pointing at the displayed first mark,
        acquire at least two outside scene images corresponding to left and right eyes of the user, and
        guide the user to point at the first mark:
        calculate the first gazing point coordinate on the basis of a position at which the user points to the first mark in the acquired at least two outside scene images:
        detect a first shift between the first standard coordinate and the first dazing point coordinate,
        display a second mark out of the plurality of marks at a predetermined second standard coordinate on the image display,
        calculate a second gazing point coordinate at which a user gazes at the second mark after displaying of the second mark based on the user's hand pointing at the displayed second mark,
        guide the user to point at the second mark,
        calculate the second gazing point coordinate on the basis of a position at which the user points to the second mark in the acquired at least two outside scene images:
        detect a second shift between the second standard coordinate and the second gazing point coordinate, and
        calculate a correction amount for controlling the display of the virtual image in the image display based on either: (i) an average shift that is calculated based on the first shift and the second shift, or (ii) out of the first shift and second shift, a shift is selected that is closest to a position in which the user visually recognizes the virtual object.

2. The head-mounted display device according to claim 1, wherein the processor calculates, as the average or selected shift between the standard coordinate and the gazing point coordinate, an angle difference between a standard vector connecting a coordinate of the mark in image data transmitted to the image display and the standard coordinate and a gazing point vector connecting the coordinate of the mark in the image data transmitted to the image display and the gazing point coordinate.

3. The head-mounted display device according to claim 2, wherein the angle difference includes an angle difference of a roll angle, an angle difference of a pitch angle, and an angle difference of a yaw angle.

4. The head-mounted display device according to claim 1, wherein
    the processor repeatedly executes, with respect to a different plurality of marks having a different plurality of standard coordinates, the steps of causing the user to visually recognize the mark on the standard coordinate, calculating the gazing point coordinate, and detecting a shift between the standard coordinate and the gazing point coordinate, and
    the processor uses, in the arrangement of the virtual object, the detected plurality of shifts concerning the different plurality of standard coordinates.

5. The head-mounted display device according to claim 4, wherein the processor executes the steps using, as the mark, any indication formed by any application in the head-mounted display device.

6. The head-mounted display device according to claim 1, wherein the processor causes, by providing a parallax between the virtual image visually recognized by the user with a right eye and the virtual image visually recognized by the user with a left eye, the user to visually recognize the first mark on the first standard coordinate and the second mark on the second standard coordinate.

7. The head-mounted display device according to claim 1, wherein the processor is further programmed to correct a display position of the first mark based on the detected shift.

8. The head-mounted display device according to claim 7, wherein the processor is further programmed to correct the display position when a coordinate of the standard coordinate is different from a coordinate of the gazing point coordinate.

9. The head-mounted display device according to claim 1, further comprising:
    a memory storing the predetermined standard coordinate at which the first mark is displayed in the image display.

10. A method of controlling a head-mounted display device, the method comprising:
    displaying, by an image display in the head-mounted display device, a virtual image having a first mark out of a plurality of marks at a predetermined first standard coordinate;
    calculating a first gazing point coordinate at which a user gazes at the first mark after displaying of the first mark based on the user's hand pointing at the displayed first mark;
    acquiring at least two outside scene images corresponding to left and right eyes of the user; and
    guiding the user to point at the first mark;

calculating the first gazing point coordinate on the basis of a position at which the user points to the first mark in the acquired at least two outside scene images;

detecting a first shift between the first standard coordinate and the first gazing point coordinate;

displaying a second mark out of the plurality of marks at a predetermined second standard coordinate on the image display;

calculating a second gazing point coordinate at which a user gazes at the second mark after displaying of the second mark based on the user's hand pointing at the displayed second mark;

guiding the user to point at the second mark;

calculating the second gazing point coordinate on the basis of a position at which the points to the second mark in the acquired at least two outside scene images;

detecting a second shift between the second standard coordinate and the second gazing point coordinate; and calculating a correction amount for controlling the display of the virtual image in the image display based on either: (i) an average shift that is calculated based on the first shift and the second shift, or (ii) out of the first shift and second shift, a shift is selected that is closest to a position in which the user visually recognizes the virtual object.

11. The method according to claim 9, further comprising: correcting a display position of the first mark based on the detected shift.

12. The method according to claim 11, further comprising:

correct the display position when a coordinate of the standard coordinate is different from a coordinate of the gazing point coordinate.

13. The method according to claim 9, further comprising: storing, in a memory, the predetermined standard coordinate at which the first mark is displayed in the image display.

14. A non-transitory computer-readable medium that stores a computer program for causing a computer to perform steps comprising:

displaying, by an image display in a head-mounted display device, a virtual image having a first mark out of a plurality of marks at a predetermined first standard coordinate;

calculating a first gazing point coordinate at which a user gazes at the first mark after displaying of the first mark based on the user's hand pointing at the displayed first mark;

acquiring at least two outside scene images corresponding to left and right eyes of the user; and guiding the user to point at the first mark;

calculating the first gazing point coordinate on the basis of a position at which the user points to the first mark in the acquired at least two outside scene images;

detecting a first shift between the first standard coordinate and the first dazing point coordinate;

displaying a second mark out of the plurality of marks at a predetermined second standard coordinate on the image display;

calculating a second gazing point coordinate at which a user dazes at the second mark after displaying of the second mark based on the user's hand pointing at the displayed second mark;

guiding the user to point at the second mark;

calculating the second gazing point coordinate on the basis of a position at which the user points to the second mark in the acquired at least two outside scene images;

detecting a second shift between the second standard coordinate and the second gazing point coordinate; and calculating a correction amount for controlling the display of the virtual image in the image display based on either: (i) an average shift that is calculated based on the first shift and the second shift, or (ii) out of the first shift and second shift, a shift is selected that is closest to a position in which the user visually recognizes the virtual object.

15. The non-transitory computer-readable medium according to claim 14, further comprising:

correcting a display position of the first mark based on the detected shift.

16. The non-transitory computer-readable medium according to claim 15, further comprising:

correcting the display position when a coordinate of the standard coordinate is different from a coordinate of the gazing point coordinate.

17. The non-transitory computer-readable medium according to claim 14, further comprising:

storing, in a memory, the predetermined standard coordinate at which the first mark is displayed in the image display.

* * * * *